United States Patent
Xu et al.

(10) Patent No.: US 9,657,337 B2
(45) Date of Patent: May 23, 2017

(54) REACTION BUFFER FOR MICROARRAY

(75) Inventors: Leon Xu, Shanghai (CN); Zhenhong Sun, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 870 days.

(21) Appl. No.: 12/520,987

(22) PCT Filed: Dec. 29, 2006

(86) PCT No.: PCT/CN2006/003650
§ 371 (c)(1),
(2), (4) Date: Apr. 21, 2010

(87) PCT Pub. No.: WO2008/080254
PCT Pub. Date: Jul. 10, 2008

(65) Prior Publication Data
US 2010/0197517 A1    Aug. 5, 2010

(51) Int. Cl.
*C12Q 1/68* (2006.01)
*C12P 19/34* (2006.01)

(52) U.S. Cl.
CPC ........... *C12Q 1/6837* (2013.01); *C12Q 1/686* (2013.01)

(58) Field of Classification Search
CPC .............................. C12Q 1/686; C12Q 1/6876
See application file for complete search history.

(56) References Cited

U.S. PATENT DOCUMENTS

| | | |
|---|---|---|
| 5,691,146 A | 11/1997 | Mayrand |
| 6,194,146 B1 | 2/2001 | Utermohlen et al. |
| 6,395,518 B1 | 5/2002 | Mayrand |
| 6,485,903 B1 | 11/2002 | Mayrand |
| 6,753,145 B2 | 6/2004 | Holcomb et al. |
| 6,902,900 B2 | 6/2005 | Davies et al. |
| 7,141,371 B2 | 11/2006 | Liu |
| 2004/0171131 A1* | 9/2004 | Feder et al. ............... 435/226 |
| 2005/0123940 A1* | 6/2005 | Sorge et al. ............. 435/6 |
| 2006/0051796 A1 | 3/2006 | Boell et al. |
| 2006/0088844 A1 | 4/2006 | Xu |
| 2006/0223075 A1* | 10/2006 | Davis et al. ............ 435/6 |
| 2007/0134661 A1 | 6/2007 | Gao et al. |
| 2009/0156415 A1* | 6/2009 | Remacle ........... C12Q 1/6837 506/9 |

FOREIGN PATENT DOCUMENTS

| | | |
|---|---|---|
| CN | 1334871 A | 2/2002 |
| CN | 1566366 A | 1/2005 |
| CN | 1661104 A | 8/2005 |
| CN | 1233847 C | 12/2005 |
| CN | 1746314 A | 3/2006 |
| EP | 1138761 A1 | 10/2001 |

OTHER PUBLICATIONS

Applied Biosystems Tm calculator, available online, http://www6.appliedbiosystems.com/support/techtools/calc/ Results for GAPDH-F and GAPDH-R primers, calculated May 13, 2013.*
"International Application Serial No. PCT/CN2006/003650, International Search Report mailed Apr. 5, 2007", 4 pgs.
"International Application Serial No. PCT/CN2006/003650, Written Opinion mailed Apr. 5, 2007", 7 pgs.
"Chinese Application Serial No. 200680056806.6, Office Action mailed Jan. 25, 2011", (w/ English Translation), 10 pgs.
"Chinese Application Serial No. 200680056806.6, Response filed Jun. 8, 2011 to Office Action mailed Jan. 25, 2011", 3 pgs.
"Chinese Application Serial No. 200680056806.6, Office Action mailed Apr. 1, 2012", (w/ English Translation), 10 pgs.
"Chinese Application Serial No. 200680056806.6, Response filed Jul. 14, 2012 to Office Action mailed Apr. 1, 2012", 4 pgs.
"Chinese Application Serial No. 200680056806.6—Office Action Received", 8 pgs.
"Chinese Application Serial No. 200680056806.6 , Response ffiled Jun. 3, 2013 to Office Action mailed Apr. 17, 2013", 3 pgs.
"Chinese Application Serial No. 201310507116.X, Office Action mailed Aug. 22, 2014", 6 pgs.
"Chinese Application Serial No. 201310507116.X, Office Action mailed Mar. 20, 2015", (w/ English Translation), 12 pgs.
"Chinese Application Serial No. 201310507116.X, Reexamination Notice mailed Nov. 28, 2016", (w/ English Translation), 10 pgs.
"Chinese Application Serial No. 201310507116.X, Response filed Mar. 6, 2015 to Office Action mailed Aug. 22, 2014", (w/ English Translation of Claims), 5 pgs.
"Chinese Application Serial No. 201310507116.X, Response filed Aug. 3, 2015 to Office Action mailed Mar. 20, 2015", (w/ English Translation of Claims), 9 pgs.

* cited by examiner

*Primary Examiner* — David Thomas
(74) *Attorney, Agent, or Firm* — Schwegman Lundberg & Woessner, P.A.

(57) ABSTRACT

Embodiments of the present invention relate to a buffer composition for an integrated nucleic acid amplification and hybridization reaction. The buffer comprise about 50-200 mM of a salt, about 10-30 mM Tris-HCl, about 2-10M Water soluble magnesium salt, about 0.05-1.5% surfactant, about 0.05-0.15 mg/ml stabilizing protein about 50-300 nM of one or more primers, about 20-150 uM of one or more dNTPs, about 5-15% glycerine, about 0.5-1.5% formamide and at least about 5 unit/ml polymerase.

5 Claims, 1 Drawing Sheet

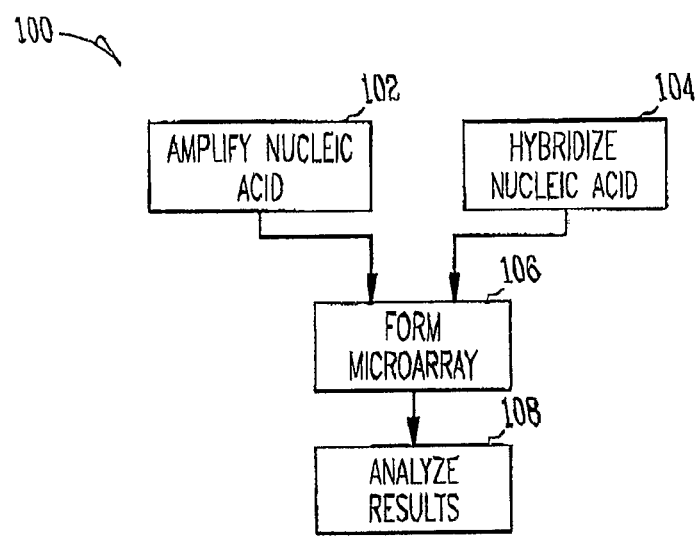

REACTION BUFFER FOR MICROARRAY

TECHNICAL FIELD

Embodiments of the present invention relate to a buffer for use with a microarray. More specifically, embodiments of the present invention relate to a buffer for the integrated reaction of nucleic acid amplification and hybridization for use with a microarray.

BACKGROUND

Nucleic acid amplification techniques provide powerful tools for the study of genetic material. The polymerase chain reaction (PCR) is one of the more frequently utilized techniques and has applications in cloning, analysis of genetic expression, DNA sequencing, genetic mapping, drug discovery and criminal forensics, among others.

For many applications, in addition to amplifying a target nucleic acid sequence, it may be useful to further characterize the sequence by treatment with a nucleic acid hybridization probe. An example of a probe would be a labeled single stranded polynucleotide which is complementary to all or part of the target sequence. Probe hybridization may provide additional sequence selectivity over simple PCR amplification as well as allowing for the characterization of multiple sequence sites within the target nucleic acid sequence in an independent manner.

Traditionally, PCR and probe hybridization processes have been performed as separate reactions. More recently, the separate reactions have been integrated into a single reaction using a single reagent mixture containing both nucleic acid amplification reagents and hybridization reagents. Some of the many advantages of combining the reactions include reducing the reagent addition steps and utilizing fewer reagents.

Methods for the simultaneous analysis of multiple genes are in ever growing demand. Microarrays are an ideal platform for such analysis in scientific, clinical and environmental contexts, since their miniature size allows one to arrange up to hundreds or thousands of biological probes in a relatively small space and reaction volume. A microarray is a collection of microscopic DNA spots attached to a solid surface, forming an array for the purpose of expression profiling (monitoring expression levels for thousands of genes simultaneously). The combined nucleic acid amplification and hybridization reaction can be utilized with microarray applications for optimal analysis.

Currently, buffers used to host the combined reaction facilitate higher reaction temperatures, which cause expansion and the potential for leakage in reaction vessels. The higher temperature reaction may also create bubbles that interfere with the recognition of hybridization signals.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 illustrates a block flow diagram of a method 100 of a method for detection or quantification of a nucleic acid, according to some embodiments.

SUMMARY

Embodiments of the present invention relate to a buffer composition for an integrated nucleic acid amplification acid hybridization reaction. The buffer comprises about 50-200 mM of a salt, about 10-30 mM Tris-HCl, about 2-10 mM water soluble magnesium salt, about 0.05-1.5% surfactant, about 0.05-0.15 mg/ml stabilizing protein, about 50-300 nM of one or more primers, about 20-150 uM of one or more dNTPs, about 5-15% glycerine, about 0.5-1.5% formamide and at least about 5 unit/ml polymerase. Embodiments also relate to methods for the detection or quantification of a nucleic acid.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the invention relate to a buffer for use in an integrated nucleic acid amplification and hybridization reaction for use with a microarray. The buffer composition provides the reagents and pH environment to successfully run both reactions for use with a microarray. Further, the buffer reduces the anneal temperature by about 8 to about 10 degrees Centigrade in the nucleic acid amplification reaction which increases effective sealing during the reaction and lessens the chance of leakage due to expansion. The buffer according to the embodiments of the invention has higher hybridization efficiency compared with currently utilized buffers. Moreover, the DNA denaturalization temperature with the buffer may be about 5-10 degrees Centigrade degree lower than with traditional buffers. The lowered temperature facilitates reaction chamber sealing and hybridization signal analysis, because higher temperatures increase the expansion pressure which increases the risk of reaction buffer leakage.

Referring to FIG. 1, a block flow diagram of a method 100 for detection or quantification of a nucleic acid is shown, according to some embodiments. Nucleic acid may be amplified 102 in the same buffer in which the nucleic acid may be hybridized 104. The integrated reaction may be used to produce nucleic acid samples to form 106 a microarray. The microarray results may then be analyzed 108.

Nucleic acid amplification 102 may be a polymerase chain reaction (PCR), for example. The nucleic acid fragment to be amplified may be determined by selecting primers. Primers are short, artificial nucleic acid strands that are complementary to the beginning or the end of the nucleic acid fragment to be amplified. They anneal by adhering to the nucleic acid template at these starting and ending points, where the nucleic acid polymerase binds and begins the synthesis of the new nucleic acid strand.

The choice of the length of the primers and their melting temperature (Tm) depends on a number of considerations. The melting temperature of a primer may be defined as the temperature at which half of the primer binding sites are occupied. Primers that are too short would anneal at several positions on a long nucleic acid template, which would result in non-specific copies. Conversely, the length of a primer is limited by the maximum temperature allowed to be applied in order to melt it, as melting temperature increases with the length of the primer. Melting temperatures that are too high may cause problems since the nucleic acid polymerase may be less active at such temperatures. The length of a primer may be generally from about 15 to about 40 nucleotides with a melting temperature between about 55° C. and about 65° C., for example.

The PCR process usually consists of a series of twenty to thirty-five cycles. Each cycle may consist of the following procedure. The double-stranded nucleic acid, such as DNA, may be heated to a temperature sufficient to denature the nucleic acid sample, or separate the strands. The temperature may be about 94-98° C., for example. Prior to the first cycle, the nucleic acid may be denatured for an extended time to ensure that both the template nucleic acid and the primers have completely separated and are then single-strand only. In addition, certain polymerases may be activated at this step.

After separating the nucleic acid strands, the temperature may be lowered so the primers can attach themselves to the single nucleic acid strands, called annealing. The annealing temperature depends on the primers and may typically be about 5° C. below the melting temperature of the primers. Embodiments of the present invention provide a buffer that may lower the annealing temperature by about 8° C. to about 10° C., for example, which facilitates sealing. A wrong temperature during the annealing step can result in primers not binding to the template nucleic acid at all, or binding at random.

The nucleic acid polymerase ultimately may copy the nucleic acid strands. It may begin at the annealed primer and work along the nucleic acid strand, called elongation. The elongation temperature may depend on the nucleic acid polymerase. Tag polymerase may elongate at a temperature of about 72 degrees Celsius, for example. The time for this stop may depend both on the nucleic acid polymerase itself and on the length of the nucleic acid fragment to be amplified. A final elongation step may be used after the last cycle to ensure that any remaining single stranded nucleic acid is completely copied.

Hybridization 104 may include probe hybridization, for example. A hybridization probe may be a short piece of nucleic acid, such as DNA, that is denatured into single strands and then radioactively labeled, such as with phosphorus, for example. The radioactive phosphorus may be incorporated into the phosphate group of the individual nucleotides of the nucleic acid, which are incorporated into the backbone of the nucleic acid strands by incubation with a polymerase enzyme. This may create a short piece of radioactively labeled nucleic acid with known sequence that will hybridize with any complementary nucleic acid strands. The probe may be used in a Northern or Southern blot to detect genes or RNA transcripts with which it has homology, a region with similar base pair sequence. The location of the hybridization probe may be determined by utilization of a microarray. For example, the buffer may contain radioactively or fluorescently-tagged dNTPs (dNTPs having a fluorescent dye molecule attached to them) so that upon completion of each PCR cycle, the nucleic acids produced are radioactive or fluorescent.

A microarray may include a collection of microscopic nucleic acid spots, generated by the integrated reaction of the embodiments of the invention, attached to a solid surface, such as glass, plastic or silicon chip, for example. The microarray may be formed for the purpose of expression profiling, such as monitoring expression levels for thousands of genes simultaneously.

Real-time PCR and hybridization may be utilized to simultaneously quantify and amplify a specific part of a given nucleic acid molecule. It may be used to determine whether or not a specific sequence is present in the sample, and if it is present, the number of copies in the sample, for example. The buffer may be utilized in a real-time PCR microarray, such as described in commonly owned U.S. Patent Application Publication No. 2006/0088844, entitled "Real-time PCR microarray based on evanescent wave biosensor," filed Apr. 27, 2006, the disclosure of which is incorporated herein in its entirety.

In addition to the target nucleic acid sequence and hybridization probes, the buffer utilized for the integrated reaction may include at least an aqueous buffer, salts, at least four deoxyribonucleotide triphosphates (dNTPs), oligonucleotide primers and a polynucleotide polymerase, for example. The buffer may further include additional components to assist with the reaction, such as surfactants, detergents, stabilizing proteins, etc. An example of an aqueous buffer may include Tris-HCl, for example. Salts may include a water soluble magnesium salt, including magnesium chloride, for example. The buffer reaction may also include glycerine and formamide, useful in the hybridization process for decreasing nucleic acid denaturalization temperature.

Deoxyribonucleotide triphosphates (dNTPs) may include thymidine triphosphates (dTTP), deoxyadenosine (dATP), deoxycitidine triphosphates (dCTP) or deoxyguanosine triphosphates (dGTP), among others, for example. Primers may include synthetic oligonuclietides that are about 10-40 bases.

An example of a reaction buffer may include about 100 mM KCl, about 20 mM Tris-HCl, about 5 mM $MgCl_2$, about 0.1% Triton X100, about 0.1 mg/ml BSA, about 100-200 nM of one or more primers, about 100 uM of one or more dNTP, about 10% glycerine, about 1% formamide and about 10 unit/ml Taq DNA polymerase, for example.

The amount of potassium chloride (KCl) may be about 50 mM to about 150 mM, for example. The amount of aqueous buffer, such as Tris-HCl, may be about 10 mM to about 30 mM, for example. The amount of magnesium chloride ($MgCl_2$) may be about 2 mM to about 10 mM, for example. The amount of surfactant or detergent, such as Triton X100, may be about 0.5% by weight to about 1.5% by weight, for example. The amount of the optional stabilizing protein, such as bovine serum albumin (BSA), may be about 0.05 mg/ml to about 0.15 mg/ml, for example. The amount of glycerine and formamide may be about from 5% to about 15% and about 0.5% to about 1.5%, respectively. The amount of glycerine and formamide may be by weight or by volume, for example. The amount of primers can vary depending on the number, but may be about 50 nM to about 300 nM, for example. The amount of dNTP may be about 50 uM to about 150 uM, for example. The mount of polymerase may be at least about 5 unit/ml, for example.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A method for the detection or quantification of a nucleic acid in an integrated nucleic acid amplification and hybridization reaction performed within a microarray, the method comprising:
   selecting one or more primer(s), each with a length between 15 and 40 nucleotides and a melting temperature between about 55 degrees Celsius and about 65 degrees Celsius;
   amplifying a nucleic acid with the one or more primer(s) in a buffer, where the amplifying comprises cycles of:
      denaturing the nucleic acid in the buffer by increasing the temperature of the nucleic acid in the buffer to a first temperature of 94-98° C.;
      annealing the nucleic acid and the one or more primer(s) in the buffer by decreasing the first temperature to a second temperature, the second temperature 5° C. below the melting point of the primer(s); and
      elongating the annealed nucleic acid by increasing the second temperature to a third temperature of 72° C.; and
   hybridizing the amplified nucleic acid in the buffer to probes within the microarray; and wherein the buffer comprises:
      about 100 mM KCl;
      about 20 mM Tris-HCl;
      about 5 mM $MgCl_2$;
      about 0.1% triton X-100;
      about 0.1 mg/ml BSA;
      about 100-200 nM of the one or more primers;
      about 100 μM of one or more dNTPs;
      about 10% glycerine;
      about 1% formamide; and
      about 10 units/ml polymerase.

2. The method of claim 1, further comprising analyzing the microarray.

3. The method of claim 1, wherein the microarray is configured for expression profiling.

4. The method of claim 1, wherein the one or more dNTPs comprise thymidine triphosphate (dTTP), deoxyadenosine (dATP), deoxycytidine triphosphate (dCTP), deoxyguanosine triphosphate (dGTP) or combinations thereof.

5. The method of claim 1, wherein the polymerase comprises Taq polymerase.

* * * * *